United States Patent [19]

Bardos et al.

[11] Patent Number: 4,544,501
[45] Date of Patent: Oct. 1, 1985

[54] BIS(2,2-DIMETHYL-1-AZIRIDINYL)PHOSPHINIC AMIDES FOR USE IN THE TREATMENT OF TUMORS

[75] Inventors: Thomas J. Bardos, Snyder; Michael E. Perlman, Bronxville; Joan E. MacDiarmid, Amherst, all of N.Y.

[73] Assignee: The Research Foundation of State University of New York, Albany, N.Y.

[21] Appl. No.: 484,213

[22] Filed: Apr. 12, 1983

Related U.S. Application Data

[63] Continuation-in-part of Ser. No. 367,338, Apr. 12, 1982.

[51] Int. Cl.[4] .................. C07D 203/06; A61K 31/395
[52] U.S. Cl. ............................................. 260/239 EP
[58] Field of Search .................. 260/239 EP; 424/200

[56] References Cited

U.S. PATENT DOCUMENTS 3,201,313  8/1965  Bardos et al. ........................ 424/200

FOREIGN PATENT DOCUMENTS 715861  9/1954  United Kingdom .
729586  5/1955  United Kingdom .
864021  3/1961  United Kingdom .
906428  9/1962  United Kingdom .

OTHER PUBLICATIONS

Lalka et al., J. Pharm. Science, 62(8) (1973), pp. 1294-1298.
Chem. Abstracts 67:21748y (1967).
Chernov et al., Chem. Abstracts, vol. 62, (1965), Abst:15243d.
Orrie et al., Chem. Abstracts, vol. 59, (1963), Abst:6337a.
Wodinsky et al., Combined Therapy with an Aziridine Derivative NSC 200724 (Ab182) and Radiation on an Experimental Leukemia, Int. J. Radiation Oncology Biol. Phys., vol. 5, pp. 1677-1680, 1979.
Hsiao et al., Synthesis of New Bis(1-Aziridinyl)Phosphinate Alkylating Agents Containing O-Phenyl N-Phenylcarbamate Side Chains, Jour. of Med. Chem., vol. 16, p. 391, 1973.
Wampler et al., Absence of Cross-Resistance to Alkylating Agents in Cyclophosphamide-Resistant L1210 Leukemia, Europ. J. Cancer, vol. 14, pp. 977-982, 1978.
Bardos et al., Synthesis of Potential Dual Antagonists III, Jour. of Pharmaceutical Sciences, vol. 54, No. 2, Feb., 1965.
Chmielewicz et al., Synthesis and Chemotherapeutic Effects of Ethyl Bis-(2,2-Dimethyl)-Ethylenamido Phosphate. A Preliminary Report, Jour. of Pharmaceutical Sciences, vol. 56, No. 9, Sep. 1967.
Bardos et al., Structure-Activity Relationships of Alkylating Agents in Cancer Chemotherapy, Annals of The New York Academy of Sciences, vol. 163, Article 2, pp. 1006-1025, Oct. 3, 1969.
Chmielewicz et al., Alterations of Some Macromolecular and Biochemical Properties of Calf Thymus DNA Caused by "Dual Antagonists" and Nitrogen Mustard, Cancer Research, 27, pp. 1248-1257, Jul. 1967.
Munson et al., Preparation and Antitumor Activity of Tris(2,2-Dimethyl-1-Aziridinyl)Phosphine Oxide (TEPA-132), Cancer Chemotherapy Reports, vol. 51, No. 5, pp. 253-259, Sep. 1967.
Bardos et al., Effects of Ring-C-Methyl Substituents on the Chemical and Biological Activities of Ethylenimine Type Alkylating Agents, Int. Congress of Chemotherapy, Jun. 1967.
Bardos, Antimetabolites: Molecular Design and Mode of Action, Topics in Current Chemistry, vol. 52, pp. 90 and 91 only, 1974.
Lalka et al., Cyclophosphamide, 2,2-Dimethyl-Aziridines and Other Alkylating Agents as Inhibitors of Serum Cholinesterase, Biochemical Pharmacology, vol. 24, pp. 455-462, 1975.
Lalka et al., Reactions of 2,2-Dimethyl-Aziridine-Type Alkylating Agents in Biological Systems II: Comparative Pharmacokinetics in Dogs, Jour. of Pharmaceutical Sciences, vol. 64, No. 2, Feb., 1975.
Bardos et al., Chemical Mechanism of the Radiation Potentiating Effects of 2,2-Dimethylaziridine-Type Antitumor Agents, Int. J. Radiation Oncology Biol. Phys., vol. 5, pp. 1653-1656, 1979.
Wampler et al., Radiation Potentiating Effect of Ethyl Bis(2,2-Dimethyl-1-Aziridinyl)Phosphinate (AB-163), Int. J. Radiation Oncology Biol. Phys., vol. 5, pp. 1681-1683, 1979.
Hsiao et al., Synthesis of 5'-Thymidinyl Bis(-1-Aziridinyl)Phosphinates as Antineoplastic Agents, Jour. of Med. Chemistry, vol. 24, pp. 887-889, 1981.
Zhdanov et al., Biologically Active Stable Radicals; XV[1]. Spin-Labeled Alkyl Carbamate-N-Phosphonic Acid Aziridides, "Synthesis", pp. 269-271, 1979.

(List continued on next page.)

Primary Examiner—Donald G. Daus
Assistant Examiner—William A. Teoli, Jr.
Attorney, Agent, or Firm—Michael L. Dunn; William J. Crossetta

[57]  ABSTRACT

Novel bis(2,2-dimethyl-1-aziridinyl)phosphinic amide antineoplastic agents are disclosed of the formula:

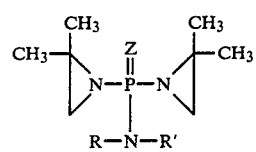

wherein R and R' are each, independently, hydrogen, alkyl, substituted alkyl, phenyl and substituted phenyl and, Z is oxygen or sulfur.

6 Claims, No Drawings

OTHER PUBLICATIONS

Konieczny et al., Methods for the Preparation of Spin-Labeled Phosphorus Compounds and Applications of Some of Them to Phosphorylative Spin-Labeling, "Synthesis", Sep. 1981.

Kimler et al., Development and Testing of New Hypoxic Cell Radiosensitizers, Radiology, vol. 33, pp. 515-517, 1979.

Bardos et al., Synthesis of Potential Dual Antagonists IV, Jour. of Pharmaceutical Sciences, vol. 54, No. 3, Mar., 1965.

Hsiao et al., Synthesis of Bis(Aziridinyl)Phosphinyl-N-Hydroxy-Urethane Derivatives as Antineoplastic Agents, Jour. of Medical Chemistry, vol. 18, p. 195, 1975.

Bardos et al., Combination of Chemotherapy with Dual Antagonists and Radiotherapy in the Treatment of Neoplastic Disease, Journal of Surgical Oncology 3(4); pp. 431-441, 1971.

BIS(2,2-DIMETHYL-1-AZIRIDINYL)PHOSPHINIC AMIDES FOR USE IN THE TREATMENT OF TUMORS

This application is a continuation-in-part of U.S. Ser. No. 367,338, filed Apr. 12, 1982.

TECHNICAL FIELD

This invention relates to phosphoraziridine amide compositions and to their use as antineoplastic agents. The invention more particularly relates to novel phosphoraziridine amide compositions having use in controlling leukemia and tumors. The compositions also find utility as antibacterials and certain of the compositions may find utility as other pesticides such as fungicides, nematocides and other antimicrobials.

BACKGROUND ART

Cancer is a general term used when referring to any disease state that results from an abnormal uncontrolled and progressive cellular growth. There are presently three principal methods available for the treatment of cancer. These methods are surgery, radiotherapy and chemotherapy. Typically, though surgery and radiotherapy may be effective by themselves, chemotherapy is usually administered in combination therewith to assure favorable results. A common example of such a combination would be the utilization of surgery to remove a tumor followed by treatment with certain chemicals capable of controlling or eliminating remaining cells which may move through the body to seed the growth of additional tumor sites (metastasis). Thus, typically a heavy reliance is placed on chemotherapy regardless of the treatment selected.

Unfortunately, such treatment with chemicals (chemotherapy) continues to have very serious disadvantages. In particular, none of the approximately 30 drugs commonly used in cancer chemotherapy have proven to be capable of eliminating the cancer disease except in a relatively small number of isolated cases. Furthermore, most of the commonly used chemicals have very high toxicity or serious side effects relative to the dosage required to be effective against the abnormal tumor or growth (neoplasm). The use of prior art chemicals in chemotherapy, therefore, very often results in serious complications which endanger the human being or other host organism being treated. These disadvantages of cancer treating chemicals (antineoplastic drugs) continue despite the fact that many thousands of potential antineoplastic agents have been screened and tested.

Many of the effective antineoplastic agents are classified as alkylating agents, i.e. a substance which introduces an alkyl, or substituted alkyl radical into a compound in place of a hydrogen atom. In chemicals utilized for treating cancer such alkylation frequently occurs within a nucleic acid structure such as DNA or RNA of the cancer cell thus effectively preventing the cell from functioning or reproducing.

A number of such alkylating agents contain one or more aziridine rings or contain intermediate structures which can yield aziridine rings. An aziridine ring is a three-membered heterocyclic ring containing one nitrogen atom and two carbon atoms. Examples of alkylating chemicals which contain aziridine rings or contain structures which can yield aziridine rings are as follows:

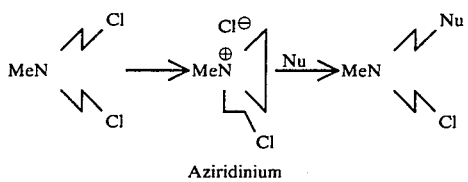

Mechanism of Nitrogen Mustard Alkylation

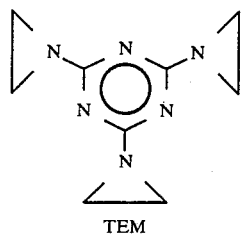

TEM

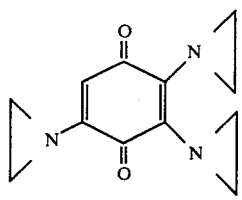

Trenimon

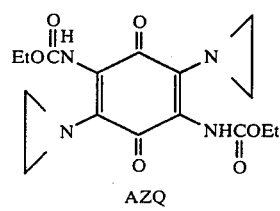

AZQ

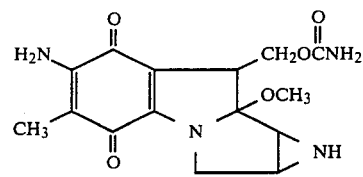

Mitomycin C

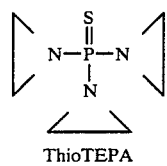

ThioTEPA

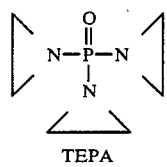

TEPA

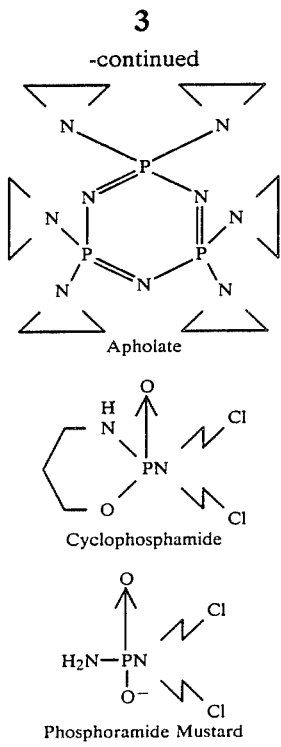

Apholate

Cyclophosphamide

Phosphoramide Mustard

These compounds are believed to open at the aziridine ring site, if they are not already open, and then combine with a biological target molecules usually a nucleic acid, or, to be susceptible to nucleophilic displacement of the nitrogen from an aziridine ring carbon by a biological taret nucleophile, such as a nucleoside base, to interrupt the replication of the nucleic acid or to interfere with messages which would be transmitted by the nucleic acid.

In addition to the Thio-TEPA and TEPA compounds, numerous other phosphoaziridines are known. Phosphoaziridines are described in numerous publications, for example, in U.S. Pat. No. 2,606,900 to Parker et al; U.S. Pat. No. 3,201,313; to Bardos et al; in the Journal of Surgical Oncology 3(4) at pp 431–441 (1971) by Bardos et al; by Kimler et al in Radiology, 133 at pp 515–517 (1979); by Bardos et al in the International Journal of Radiation Oncology Biological Physics, Volume 5 at pp 1653–1656 (1979); by Wampler et al in International Journal of Radiation Oncology Biological Physics, Volume 5 at pp 1681–1683 (1979); and by Chmielewicz et al in the Journal of Pharmaceutical Sciences, Volume 56, No. 9 at pp 1179–1181 (1967).

Initially, phosphoaziridines were considered and classified as alkylating agents. In some cases, the diaziridinyl phosphinoyl group was chemically combined through an amide linkage to ethyl carbamate in an attempt to obtain a synergistic effect between the phosphoaziridine and urethane group. Such compounds derived from unsubstituted aziridines demonstrate potent anti-tumor activity but showed no significant clinical advantage over other alkylating agents.

Bis(2,2-dimethyl-1-aziridinyl) phosphinates were subsequently developed which showed the interesting characteristic of not only being chemicals suitable for chemotherapy but demonstrated the ability to potentiate the therapeutic effects of radiation upon transplated tumors. The Bis(2,2-dimethyl-1-aziridinyl)phosphinates which are connected with urethane groups nevertheless show highly effective antitumor activity with remarkably low toxicity for inhibiting the production and development of blood cells (hematopoietic toxicity) when compared with conventional alkylating agents.

BRIEF DESCRIPTION OF THE INVENTION

In accordance with the invention, there is provided a method for inhibiting the growth of tumor cells by the direct effects of chemotherapy. In accordance with the method, compounds of the invention are used as a chemotherapeutic agent and tumor cells are exposed to an effective tumor inhibiting concentration of a compound of the invention.

The compounds useful in the method of the invention comprise two aziridine rings and have the formula:

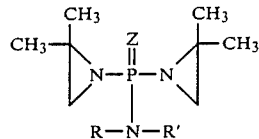

wherein R and R' are independently hydrogen, alkyl of 1–6 carbon atoms, substituted alkyl of 1–10 carbon atoms, phenyl or substituted phenyl, and, Z is oxygen or sulfur.

Novel compounds of the invention comprise those having the formula:

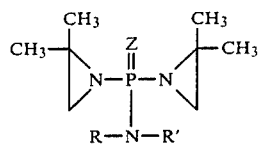

wherein R and R' are independently hydrogen, alkyl, substituted alkyl, phenyl or substituted phenyl, and Z is oxygen or sulfur provided when Z is oxygen and one of R or R' is alkyl or cycloalkyl of 4 or more carbon atoms, the other of R or R' is hydrogen, alkyl of 1–3 carbon atoms, substituted alkyl, phenyl or substituted phenyl, and when Z is sulfur, both R and R' are not methyl.

Representative alkyl groups encompassed within the description of R and R' include substituted and unsubstituted, branched, straight chain and cyclic methyl, ethyl, propyl, butyl, pentyl, cyclopentyl, hexyl, and the like, up to about 10 carbon atoms. Representative substituents for the substituted alkyl include halogen such as chlorine, iodine, fluorine and bromine, hydroxy, amine, nitro, alkoxy, phenyl, sulfonate, substituted phenyl and the like. Representative substituents for the substituted phenyl include: halogen such as chlorine, fluorine, bromine and iodine, hydroxy, nitro, alkoxy, amine, sulfonate and the like.

Typical compounds encompassed within the description of the invention include: P,P-bis(2,2-dimethyl-1-aziridinyl)-phosphinic amide; P,P-bis(2,2-dimethyl-1-aziridinyl)thiophosphinic amide; P,P-bis(2,2-dimethyl-1-aziridinyl)-N-methylphosphinic amide; P,P-bis(2,2-dimethyl-1-aziridinyl)-N,N-dimethylphosphinic amide; P,P-bis(2,2-dimethyl-1-aziridinyl)-N-(methyl)-thiophosphinic amide; P,P-bis(2,2-dimethyl-1-aziridinyl)-N,N-(dimethyl)thiophosphinic amide; P,P-bis(2,2-dimethyl-1-aziridinyl)-N-ethylphosphinic amide; P,P-bis(2,2-dimethyl-1-aziridinyl)-N-(ethyl)thiophosphinic amide; P,P-bis(2,2-dimethyl-1-aziridinyl)-N-propylphosphinic amide; P,P-bis(2,2-dimethyl-1-aziridinyl)-N-(propyl)thiophinic amide; P,P-bis(2,2-dimethyl-1-aziridinyl)-N-butylphosphinic amide; P,P-bis(2,2-dimethyl-1-aziridinyl)-N-(butyl)thiophosphinic amide; P,P-bis(2,2-dimethyl-1-aziridinyl)-N-(3-methoxy-1-propyl)phosphinic amide; P,P-bis(2,2-dimethyl-1-aziridinyl)-N-(3-(dimethylamino)-1-propyl)phosphinic amide; P,P-bis(2,2-dimethyl-1-aziridinyl)-N-phenylphosphinic amide; P,P-bis(2,2-dimethyl-1-aziridinyl)-N-(5-diethylamino-1-pentyl)phosphinic amide; P,P-bis(2,2-dimethyl-1-aziridinyl)-N-(5-(diethylamino)-2-pentyl)-phosphinic amide; P,P-bis(2,2-dimethyl-1-aziridinyl)-N-cyclohexylphosphinic amide; P,P-bis(2,2-dimethyl-1-aziridinyl)-N-(3'-methoxy-4'-nitrophenyl)phosphinic amide; P,P-bis(2,2-dimethyl-1-aziridinyl)-N-(p-chlorophenyl)phosphinic amide; P,P-bis(2,2-dimethyl-1-aziridinyl)-N-(p-fluorophenyl)phosphinic amide; P,P-bis(2,2-dimethyl-1-aziridinyl)-N-(p-dimethylaminophenyl)phosphinic amide; P,P-bis(2,2-dimethyl-1-aziridinyl)-N-(8-hydroxy-1-octyl)phosphinic amide; P,P-bis(2,2-dimethyl-1-aziridinyl)-N-benzylphosphinic amide, and the like.

The compounds of the invention can generally be prepared by the reaction of a 1:2 mole ratio of an appropriate phosphorus oxy or thio halide, such as phosphoryl chloride or phosphorus oxy bromide, with 2,2-dimethyl-1-aziridine in accord with the formula:

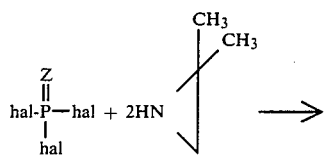

Formula 1     Formula 2

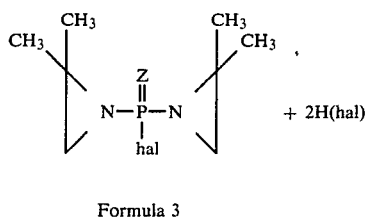

Formula 3

The resulting bis(2,2-dimethyl-1-aziridinyl)phosphinic or thiophosphinic halide is therefore reacted with an appropriate amine in the presence of an inert solvent to produce the final phosphinic amide in accordance with the formula:

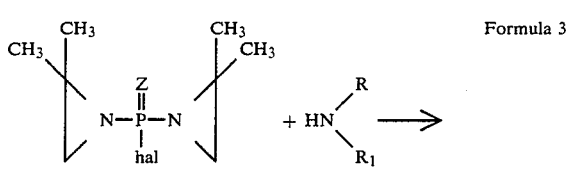

Formula 3

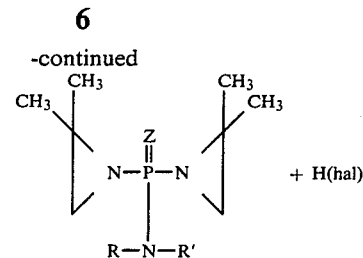

In general, the compounds of formula 3 prepared by the reaction of compounds of formula 2 with PO(Hal)$_3$ or PS(Hal)$_3$ in the presence of an appropriate halogen acceptor are achieved by the methods described in U.S. Pat. No. 3,201,313 to Bardos et al; by U.S. Pat. No. 2,606,900 to Parker et al; and, in the previously described article by Chemielewicz et al which appeared in the Journal of Pharmaceutical Science, Volume 56, No. 9, September 1967 at pages 1179–1181. The reactions are generally carried out in an inert atmosphere to avoid the presence of moisture, at temperatures from about 0° C. to about −50° C.

The 2,2-dimethyl-1-aziridine of formula 2 can be prepared by methods of the prior art for example by Wenker and Gabriel synthesis. The Wenker synthesis is described in the Journal of the American Chemical Society, Volume 57 at 2328 (1935) and the Gabriel synthesis is described in Ber. Volume 21 at page 1049(1881).

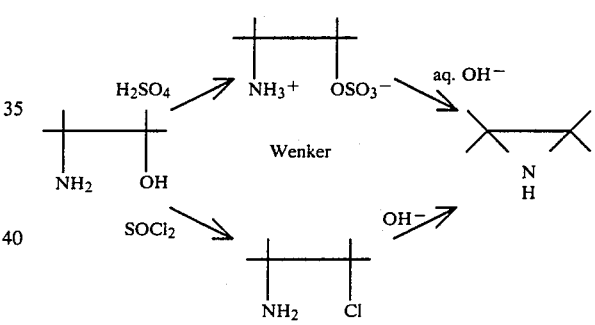

Other methods for preparation of intermediates of formula 2 are described by Derm et al in "Ethyleneimine and Other Aziridines" Academic Press, New York, 1969. A general review of methods of synthesis of intermediates of formula 2 is given by Michael Ellis Perlman, an inventor herein, in a State University of New York thesis entitled "Synthesis and Mechanistic Studies Of Phosphoraziridine As Radiation Sensitizers" the abstract of which was first published in July of 1982.

As previously discussed, the method of the invention comprises the chemical inhibition of the growth of tumor cells. In accordance with the method, an organism containing tumor cells is administered to an effective tumor inhibiting concentration of a compound having a pH of 5 or above of the formula:

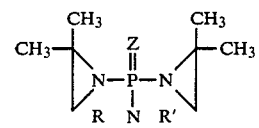

Where R and R' are each independently hydrogen, alkyl of 1 to 6 carbon atoms, substituted alkyl of 1 to 10 carbon atoms, phenyl and substituted phenyl; and Z is oxygen or sulfur.

The effective tumor inhibiting concentration of the compound of the invention usually ranges between about 0.5 and 1500 milligrams per kilogram of body weight and is preferably between about 1 and about 300 milligrams per kilogram of body weight of the organism being treated. Though the most common method of treatment is by injection other typical methods of the prior art are contemplated by the invention. After injection of the compound of the invention, sufficient time is permitted to allow the compound of the invention to collect at the tumor site.

The organisms which are treated in accordance with the method of the invention are usually mammals including human beings.

In accordance with the method of the invention, the growth of tumor cells can be chemically inhibited, with particular selectivity toward hypoxic (anaerobic) cells which is desirable since many tumors are hypoxic. A more effective and selective toxicity to tumor cells (cytotoxic) may therefore be realized, possibly with lower doses of the chemotherapeutic agent and with the likelihood of more specific localized toxic effect at the tumor site so that described incidence of toxic side effects to the overall organism may be achieved.

The following examples are meant to illustrate the invention and are not to be viewed as a limitation thereof. All temperatures are in degrees centigrade unless otherwise denoted and standard laboratory precautions were taken to avoid contamination by moisture.

EXAMPLE 1

Preparation of P,P-bis(2,2-dimethyl-1-aziridinyl)phosphinoyl chloride 0.08 moles of triethylamine, 0.025 moles of $POCl_3$ and 150 milliliter of dried tetrahydrafuran(THF) were combined in a 250 milliliter round bottom flask, under nitrogen atmosphere to avoid moisture contamination, to form a first solution which was then cooled to $-40°$ C. A second solution was prepared containing 0.05 moles of 2,2-dimethylaziridine in 20 milliliters of THF and the second solution was added dropwise to the cooled first solution over a period of about 2 hours. The resulting slurry was then warmed to room temperature, over a 1 hour period, and then filtered under a nitrogen atmosphere to remove precipitated triethylamine hydrochloride. The remaining filtrate comprised 0.025 moles of P,P-bis(2,2-dimethyl-1-aziridinyl)phosphinoyl chloride and about 170 milliliters of THF.

In a similar manner, 0.08 moles of triethylamine, 0.025 moles of $PSBR_3$ and 150 milliliters of THF are combined and treated, by dropwise addition, with a solution containing 0.05 moles of 2,2-dimethylaziridine and 20 milliliters of THF. The resulting slurry is filtered to remove precipitated triethylamine hydrobromide and the filtrate is found to comprise about 0.025 moles of P,P-bis(2,2-dimethyl-1-aziridinyl)thiophosphinic bromide.

EXAMPLE 2

Preparation of P,P-bis(2,2-dimethyl-1-aziridinyl)phosphinic amide

A solution comprising 0.02 moles of P,P-bis(2,2-dimethyl-1-aziridinyl)phosphinoyl chloride and about 170 milliliters of THF, prepared in accordance with Example 1, was placed in a dry vessel fitted with a bubbler tube for the introduction of gaseous material below the liquid surface. The vessel and contents were cooled to about $-10°$ C. and gaseous ammonia gas was bubbled into the solution until the solution appeared saturated therewith (about 1 hour). The thus saturated solution was allowed to sit overnight at $4°$ C. with constant stirring. The resulting product was filtered and the filtrate was concentrated by rotary evaporation at room temperature. The thus concentrated filtrate was recrystallized from THF providing a 65% yield of P,P-(2,2-dimethyl-1-aziridinyl)phosphinic amide which was characterized by NMR and IR as having a purity of 99%. Elemental Analysis confirmed the structure contained the following:

| Found | Calculated |
|---|---|
| C - 47.19% | 47.28% |
| H - 8.95% | 8.93% |
| N - 20.69% | 20.67% |

In a similar manner 0.025 moles of P,P-bis(2,2-dimethyl-1-aziridinyl)thiophosphinic bromide, and about 170 milliliters of THF, is saturated with gaseous ammonina gas at about $-10°$ C. and the saturated solution is allowed to sit over night with constant stirring. Upon filtration, concentration by rotary evaporation, and recrystallization, P,P-bis(2,2-dimethyl-1-aziridinyl)thiophosphinic amide is recovered at a purity in excess of about 95%.

EXAMPLE 3

Preparation of P,P-bis(2,2-dimethyl-1-aziridinyl)-N-methylphosphinic amide

A solution comprising 0.025 moles of P,P-bis(2,2-dimethyl-1-aziridinyl)phosphinoyl chloride in about 170 milliliters of THF, prepared in accordance with Example 1, was cooled to $-15°$ C. and a saturated excess of gaseous methylamine was introduced to the solution through a bubbler tube in accord with the process of Example 2. The vessel and contents were warmed to about $4°$ C. and the saturated solution was allowed to sit overnight with constant stirring at that temperature. The resulting slurry was filtered and the filtrate was concentrated by rotary evaporation at room temperature. The thus concentrated filtrate was vacuum distilled at $94°$ C. and 0.14 millimeters of mercury providing a 75% yield of P,P-bis(2,2-dimethyl-1-aziridinyl)-N-methylphosphinic amide. NMR and aziridinyl titration characterization of the product indicated a purity of 98.4%.

In a similar manner 0.025 moles of P,P-bis(2,2-dimethyl-1-aziridinyl)thiophosphinic bromide in about 170 milliliters of THF, prepared in accordance with Example 1, is saturated with an excess of gaseous methylamine, stirred over night at $4°$ C., filtered, concentrated on a rotary evaporator at room temperature, and vacuum distilled to provide about 65% yield of P,P-bis(2,2-dimethyl-1-aziridinyl)-N methylthiophosphinic amide.

EXAMPLE 4

Preparation of
P,P-bis(2,2-dimethyl-1-aziridinyl)-N,N-dimethylphosphinic amide 0.16 moles of triethylamine, 0.05 moles of $POCl_3$ and 150 milliliters of dried tetrahydrofuran were combined in a 250 milliliter round bottom flask, under a nitrogen atmosphere to avoid moisture contamination, to form a first solution which was then cooled to −40° C. A second solution was then prepared containing 0.10 moles of 2,2-dimethylaziridine in 20 milliliters of THF and the second solution was added dropwise to the cooled first addition over a period of about 2 hours. The resulting slurry was then warmed to approximately 0° C. over an hours' time and thereafter cooled again to −20° C. A third solution was then prepared containing 0.16 moles of dimethylamine in 25 milliliters of dried THF and the third solution was added dropwise to the cooled aforesaid combination of the first and second solutions over a period of about 2 hours. The vessel was sealed and stirred overnight at 4° C. The resulting slurry was then filtered, the filtrate was concentrated by rotary evaporation, and thereafter vacuum distilled at 58° C./0.15 millimeters Hg to produce a 75% yield of P,P-bis(2,2-dimethyl-1-aziridinyl)-N,N-dimethylphosphinic amide. The product was characterized by NMR and aziridine titration as having a purity of 99.45%. Elemental analysis confirmed the structure as follows:

| Found | Calculated |
|---|---|
| % C = 51.96 | 51.97 |
| % H = 9.60 | 9.59 |
| % N = 18.14 | 18.17 |

In a similar manner 0.16 moles of triethylamine, 0.05 moles of $PSBr_3$ and 150 milliliters of dried tetrahydrofuran are combined in a 250 milliliter round bottom flask which is thereafter treated with a first solution containing 0.10 moles of 2,2-dimethylaziridine in 20 milliliters of THF and a second solution containing 0.16 moles of dimethylamine in 25 millimeters of dried THF, to produce a slurry which after filtration, concentration of the filtrate and vacuum distillation affords about 65% yield of P,P-bis(2,2-dimethyl-1-aziridinyl)-N,N-dimethylthiophosphinic amide.

EXAMPLE 5

Preparation of
P,P-bis(2,2-dimethyl-1-aziridinyl)-N-(3-methoxy-1-propyl)phosphinic amide 0.08 moles of triethylamine, 0.025 moles of $POCl_3$ and 150 milliliters of dried tetrahydrofuran were combined in a 250 milliliter round bottom flask, under a nitrogen atmosphere to avoid moisture contamination, to form a first solution which was then cooled to −40° C. A second solution was then prepared containing 0.05 moles of 2,2-dimethylaziridine in 20 milliliters of THF and the second solution was added dropwise to the cooled first solution over a period of about 2 hours. The resulting slurry was then warmed over a period of about 1 hour to 0° C. then cooled again to −30° C. and then had added thereto, by dropwise addition, a solution containing 0.026 moles of 3-methoxypropyl amine in 20 milliliters of THF. The solution was then allowed to stand overnight with constant stirring at ambient temperature, the resulting slurry was filtered, the filtrate was concentrated by rotary evaporation, and thereafter vacuum distilled at 130° C./0.42 millimeters Hg to produce a 60% yield of 3-methoxypropylamino phosphoraziridine. NMR characterization indicated that the product was 95% pure.

EXAMPLE 6

Preparation of
P,P-bis(2,2-dimethyl-1-aziridinyl)-N-(3-dimethylaminopropyl)phosphinic amide A solution containing 0.025 moles of P,P-bis(2,2-dimethyl-1-aziridinyl)phosphinyl chloride in about 170 milliliters of THF was prepared in accordance with Example 1, chilled to −40° C. and treated, by slow dropwise addition, with a solution containing 0.026 moles of 3-dimethylaminopropylamine, in 25 milliliters of THF. The resulting slurry was stirred overnight at ambient temperature, filtered, the filtrate was concentrated by rotary evaporation, and vacuum distilled at 119° C./0.45 millimeter of mercury to produce a 40% yield of P,P-bis(2,2-dimethyl-1-aziridinyl)-N-(3-dimethylaminopropyl)phosphinic amide. NMR characterization confirmed the product was 99% pure. Elemental analysis confirmed the structure contained the following:

| Found | Calculated |
|---|---|
| % C = 53.89 | 54.14 |
| % H = 10.17 | 10.14 |
| % N = 19.38 | 19.43 |

In a similar manner 0.025 moles of P,P-bis(2,2-dimethyl-1-aziridinyl)thiophosphinic bromide and about 170 ml of THF are treated by dropwise addition with 0.02 moles of 3-dimethylaminopropyl amine in 25 millimeters of THF stirred for several hours at ambient temperature, filtered, concentrated by rotary evaporation, and vacuum distilled to produce about 35% yield of P,P-bis(2,2-dimethyl-1-aziridinyl)-N-(3-dimethylaminopropyl)thiophosphinic amide.

In a similar manner 0.025 moles of P,P-bis(2,2-dimethyl-1-aziridinyl)phosphinoyl chloride in about 170 ml of THF are treated by dropwise addition with 0.026 moles of 5-diethylaminopentylamine in 25 ml of THF, stirred for several hours at ambient temperature, filtered, concentrated by rotary evaporation and vacuum distilled to yield about 90% pure P,P-bis(2,2-dimethyl-1-aziridinyl)-N-(5-diethylamino-1-pentyl)phosphine amide.

EXAMPLE 7

Preparation of
P,P-bis(2,2-dimethyl-1-aziridinyl)phosphoric anilide 0.025 moles of $POCl_3$ and 0.079 moles of trimethylamine was combined with 150 milliliters of THF, cooled to −40° C. and added over a 1 hour period, by dropwise addition, to a solution containing 20 milliliters of THF and 0.025 moles of aniline. The slurry was allowed to warm slowly to 10° C., over a 1 hour period and is then treated, by dropwise addition, with a solution containing 0.05 moles of 2,2-dimethylaziridine in 20 milliliters of THF. The slurry was allowed to warm to ambient temperature and was stirred overnight at this temperature. The slurry was filtered, the filtrate was concentrated at room temperature by rotary evaporation, resulting in a fine white powder in residual oils. The mixture of powder and residual oils was washed with a 10 milliliter quantity of dry ethyl ether, filtered to remove the solid product, and resulted in a 20% yield of the desired P,P-bis(2,2-dimethyl-1-aziridinyl)phosphinic anilide, which was characterized by NMR, as 99% pure.

EXAMPLE 8

Various bis(2,2-dimethyl-1-aziridinyl)phosphinic amides, prepared in accord with examples 1–7, were tested for antitumor activity in vivo using the lymphocytic leukemia P-388 in mice. The test system was that employed by the National Cancer Institute (NCI) for the primary screening of antitumor agents, according to Protocol 1.200 (Cancer Chemo. Rpts. Part 3, Vol. 3, No. 2, p. 9; 1972). In the study, $10^6$ ascites cells were implanted in the peritoneal cavity of $CDF_1$ female mice. Each amide was given in a single injection, at six or four dose levels (6 mice/dose level). The control animals received saline (10 mice). Test criteria was in accord with NCI protocol as follows: toxicity is indicated where <4/6 or <3/4 mice are alive on Day 5; antitumor activity is indicated when % T/C>125 [% T/C=(MST treated/MST control)×100, where MST=medium survival time]. The results are shown in Table I.

TABLE I

| | Anti-tumor Activity (% T/C) | | | | | |
|---|---|---|---|---|---|---|
| | Dosage Levels (Mg/Kg) | | | | | |
| Compound | 256 | 128 | 64 | 32 | 16 | 8 |
| bis(2,2-dimethyl-1-aziridinyl)phosphinic amide | 206 | 188 | 159 | 153 | 147 | 124 |
| bis(2,2-dimethyl-1-aziridinyl)N—methyl-phosphinic amide | toxic | 239 (1)* | 211 | 206 | 167 | 144 |
| bis(2,2-dimethyl-1-aziridinyl)N,N—dimethyl-phosphinic amide | toxic (1)* | 272 | 217 | 183 | 150 | 133 |
| bis(2,2-dimethyl-1-aziridinyl)N—ethyl-phosphinic amide | 288 | 225 | 206 | 188 | | |
| bis(2,2-dimethyl-1-aziridinyl)N—propyl-phosphinic amide | >363 (3)* | 231 (1)* | 194 | 194 | | |
| bis(2,2-dimethyl-1-aziridinyl)N—butyl-phosphinic amide | 238 | 200 | 188 | 175 | | |
| bis(2,2-dimethyl-1-aziridinyl)N—methoxypropyl phosphinic amide | 225 (1)* | 219 (1)* | 195 | 175 | | |
| bis(2,2-dimethyl-1-aziridinyl)N',N'—dimethyl-N—aminopropyl phosphine amide | toxic (1)* | 256 (1)* | 231 | 213 | | |
| bis(2,2-dimethyl-1-aziridinyl)N—phenyl-phosphinic amide | 169 | 138 | 144 | 144 | | |

( )* - 30 Day Survivors

What is claimed is:

1. A compound having the formula:

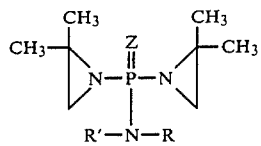

wherein R and R' are independently hydrogen, or substituted alkyl of up to about 10 carbon atoms, wherein each substituent is selected from the group consisting of amine and alkoxy, and Z is oxygen provided at least one of R or R' is substituted alkyl.

2. The compound of claim 1 of the structure

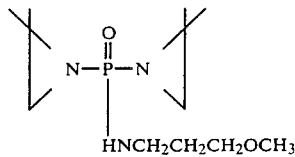

HNCH₂CH₂CH₂OCH₃

3. The compound of claim 1 of the structure

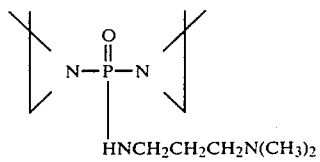

HNCH₂CH₂CH₂N(CH₃)₂

4. The compound of the structure

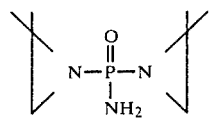

5. The compound of the structure

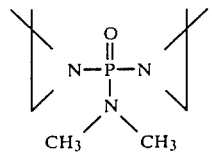

6. A compound of claim 1 of the structure

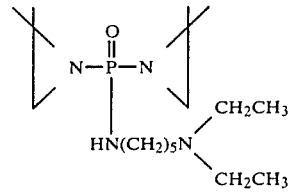

* * * * *